| (12) | United States Patent | (10) Patent No.: | US 9,289,552 B2 |
|---|---|---|---|
| | Gerlach et al. | (45) Date of Patent: | Mar. 22, 2016 |

(54) INFUSION PUMP WITH DRIVE DEVICE AND BLOCKING MECHANISM FOR THE INFUSION SYRINGE PISTON DRIVE HEAD

(71) Applicant: B. BRAUN MELSUNGEN AG, Melsungen (DE)

(72) Inventors: Hans-Josef Gerlach, Marsberg (DE); René Wildner, Melsungen (DE); Rolf Heitmeier, Baunatal (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 31 days.

(21) Appl. No.: 14/368,225

(22) PCT Filed: Dec. 20, 2012

(86) PCT No.: PCT/EP2012/076441
§ 371 (c)(1),
(2) Date: Jun. 23, 2014

(87) PCT Pub. No.: WO2013/092889
PCT Pub. Date: Jun. 27, 2013

(65) Prior Publication Data
US 2014/0343533 A1    Nov. 20, 2014

(30) Foreign Application Priority Data
Dec. 23, 2011  (EP) .................................. 11010187

(51) Int. Cl.
*A61M 5/168* (2006.01)
*A61M 5/172* (2006.01)
*A61M 5/145* (2006.01)

(52) U.S. Cl.
CPC ............. *A61M 5/172* (2013.01); *A61M 5/1454* (2013.01); *A61M 5/1456* (2013.01);
(Continued)

(58) Field of Classification Search
CPC ................. A61M 5/14212; A61M 5/14216; A61M 5/145; A61M 5/1452; A61M 5/16831; A61M 5/315; A61M 5/31501; A61M 5/31583; A61M 5/5013; A61M 5/502; A61M 2005/14506; A61M 2005/2086; A61M 2005/31508; A61M 2005/3151; A61M 2005/5033
See application file for complete search history.

(56) References Cited

U.S. PATENT DOCUMENTS

| 5,545,140 A | 8/1996 | Conereo et al. |
| 6,423,035 B1 * | 7/2002 | Das ..................... A61M 5/1456 128/DIG. 1 |

(Continued)

FOREIGN PATENT DOCUMENTS

| CN | 1490060 | 4/2004 |
| DE | 42 13 172 | 5/1993 |

(Continued)

OTHER PUBLICATIONS

International Search Report for PCT/EP2012/076441 mailed Apr. 2, 2013.

(Continued)

*Primary Examiner* — Bhisma Mehta
*Assistant Examiner* — James Ponton
(74) *Attorney, Agent, or Firm* — RatnerPrestia (57) ABSTRACT

A drive device of an infusion syringe piston drive head for moving an infusion syringe piston is described. The device includes an advancing means including an advancing slide, an advancing spindle and a multi-part advancing spindle nut having at least one radially movable nut shell, and a blocking means adapted to be automatically triggered by a control sensor for blocking an infeed motion of the drive head in which the advancing slide is drivable by the advancing spindle nut at the advancing spindle and in which the drive head is arranged at the advancing slide, wherein the blocking means adapted to be automatically triggered by a control sensor includes the multi-part advancing spindle nut for blocking the infeed motion of the drive head on the advancing spindle.

17 Claims, 3 Drawing Sheets

(52) U.S. Cl.
CPC ...... *A61M 5/14546* (2013.01); *A61M 5/16831* (2013.01); *A61M 2005/14573* (2013.01); *A61M 2205/276* (2013.01); *A61M 2205/332* (2013.01)

(56) References Cited

U.S. PATENT DOCUMENTS

| | | |
|---|---|---|
| 6,932,242 B2 | 8/2005 | Gerlach et al. |
| 2004/0057855 A1 | 3/2004 | Gerlach et al. |
| 2009/0005730 A1 | 1/2009 | Gerlach et al. |
| 2012/0215170 A1 | 8/2012 | Traversaz et al. |

FOREIGN PATENT DOCUMENTS

| | | |
|---|---|---|
| EP | 1 329 232 | 7/2003 |
| EP | 1 374 932 | 1/2004 |
| WO | WO 2011/039250 | 4/2011 |

OTHER PUBLICATIONS

Translation of Informal Comments to the International Search Report for PCT/EP2012/076441 dated Mar. 28, 2013.
Chinese First Office Action and Search Report with translation for CN 201280064083X dated Jul. 20, 2015.

* cited by examiner

INFUSION PUMP WITH DRIVE DEVICE AND BLOCKING MECHANISM FOR THE INFUSION SYRINGE PISTON DRIVE HEAD

CROSS REFERENCE TO RELATED APPLICATIONS

This application is the U.S. national phase application of PCT International Application No. PCT/EP2012/076441 filed Dec. 20, 2012, which claims priority to European Patent Application No. EP 11010187.0 filed Dec. 23, 2011, the contents of each application being incorporated by reference herein.

FIELD OF THE INVENTION

The invention relates to a drive device of a syringe pump drive head for moving an infusion syringe piston comprising an advancing means including an advancing slide, an advancing spindle and a multi-part advancing spindle nut having at least one radially movable nut shell and comprising a blocking means to be automatically triggered with a control sensor for blocking an infeed motion of the drive head in which the advancing slide can be driven with the advancing spindle nut at the advancing spindle and in which the drive head is arranged on the advancing slide.

Moreover, the invention relates to an infusion pump comprising a drive head for moving an infusion syringe piston of an infusion syringe disposed on the infusion pump, comprising an advancing means for driving the drive head and comprising a safety means for preventing inadvertent bolus administration.

Furthermore, the invention relates to a method for operating an infusion pump in which a drive head for an infusion syringe piston of an infusion syringe is advanced by an advancing means, in which a multi-part advancing spindle nut is moved along an advancing spindle for driving the drive head and in which an actuating element of a safety device is triggered to prevent inadvertent bolus administration, when the drive head is moved up to the infusion syringe piston during replacement of the infusion syringe.

BACKGROUND

Generic drive devices are well known from the state of the art and have been successfully used in infusion therapy since long.

DESCRIPTION OF THE RELATED ART

For example from WO 2011/039250 A1 a method for preventing inadvertent bolus administration with respect to a manual feed movement of a slide means for an infusion syringe piston especially after replacing an infusion syringe on an infusion pump as well as the corresponding infusion pump for this method are known. Apart from the slide means for sliding the infusion syringe piston, the infusion pump especially includes an infusion syringe seat for securing an infusion syringe, an advance comprising a two-part advancing spindle nut for driving the slide means as well as a means for blocking the manual infeed motion of the slide means. In this context, the advance excels especially by an advancing spindle and an advancing coupling for coupling and/or uncoupling the slide means with and/or from the advancing spindle, whereby in the uncoupled state of the coupling the slide means advantageously can be quickly fed manually to the infusion syringe piston of the newly inserted infusion syringe. Such quick manual feeding is of advantage especially in critical situations, when it is necessary to quickly administer a vital infusion to a patient. In order to be able to reduce the risk of quite dangerous inadvertent bolus administration to the patient, however, the infusion pump is provided with a blocking means by which the manual infeed motion can be quickly inhibited, when the slide means has been manually fed sufficiently closely to the infusion syringe piston. In particular, the blocking means excels by a check thread shaft juxtaposed to the advancing spindle and including a threaded shaft nut non-detachably corresponding thereto and by a braking means for the check thread shaft. The threaded shaft nut is tightly connected to the slide means so that the manual feed motion immediately blocks when the braking means blocks rotation of the check thread shaft. The blocking means is controlled by a signal means associated with the slide means and comprising at least one sensor which is adapted to detect an approach of the slide means to the infusion syringe piston. Hereby inadvertent or critical abutting against the infusion syringe piston in the course of quick manual infeed motion can be reliably prevented. The blocking means includes an electromagnetic brake electrically connected to the signal means for blocking the check thread shaft.

SUMMARY OF THE INVENTION

It is an object of the present invention to prevent inadvertent bolus administration to a patient especially in the course of replacement of the infusion syringe by a different structural design.

An object of the invention is achieved by a drive device of an infusion syringe piston drive head for moving an infusion syringe piston comprising an advancing means including an advancing slide, an advancing spindle and a multi-part advancing spindle nut having at least one radially movable nut shell and comprising a blocking means for blocking an infeed motion of the drive head, in which the advancing slide can be driven with the advancing spindle nut at the advancing spindle and in which the drive head is arranged at the advancing slide in which, according to aspects of the invention, the blocking means adapted to be automatically triggered with a check sensor comprises the multi-part advancing spindle nut for blocking the infeed motion of the drive head at the advancing spindle.

By the fact that the blocking means adapted to be automatically triggered by a check sensor directly comprises the multi-part advancing spindle nut the entire drive device of the drive head can be constructed in a by far simpler manner so that especially the manual infeed motion at the advancing spindle can be blocked by an extremely simple constructional design. In particular, as regards the state of the art explained in the beginning a second threaded shaft including the electromagnetic brake can be dispensed with, thus enabling a substantially more compact design of the present drive device.

In this respect, insertion of a new infusion syringe into an infusion pump is substantially facilitated and infusion syringes can thus be replaced more quickly, too. Nevertheless, the risk of bolus administration to a patient can be reliably prevented.

The term "nut shell" in accordance with the invention describes a shell part of an advancing spindle nut cut longitudinally as to its longitudinal extension, wherein the shell part can be radially raised or lifted off the advancing spindle. Preferably the advancing spindle nut includes at least two nut shells of this type so that uniform engaging contact can be ensured between the advancing spindle and the advancing spindle nut. In this way the working precision can be further increased.

Ideally the advancing spindle nut is supported or arranged on or in the advancing slide so that a robust and compact unit can be provided at the advancing means.

Preferably, the advancing spindle nut of the blocking means includes at least two nut shells, each of the at least two nut shells having a female thread adapted to correspond to a male thread of the advancing spindle, whereby the advancing spindle nut is adapted to symmetrically correspond to the advancing spindle.

In this respect, an object of the invention is also achieved by an infusion pump comprising a drive head for moving an infusion syringe piston of an infusion syringe arranged on the infusion pump, comprising an advancing means for driving the drive head and a safety means for preventing inadvertent bolus administration, wherein the infusion pump excels by a drive device according to any one of the features described here.

Advantageously the operating safety of the infusion pump is also increased due to the simpler design, as fewer components are provided and in this way especially the probability of failure can be reduced. So far the risk of uncontrolled infusion can be further significantly reduced despite quicker possibility of replacing an infusion syringe on an infusion pump.

An aspect of the present infusion pump is a syringe pump in which at least one infusion syringe can be inserted. The present infusion pump can be operated both as single pump and combined in an aligned system or a docking station.

It is understood that the blocking means can be realized in different constructional designs. For instance, most different axial shifting means can be provided as regards the blocking means. A preferred configuration variant provides, however, that the blocking means comprises an axially movable trigger sleeve which radially surrounds the advancing spindle nut on the outside, whereby the mechanical system has a particularly slim design.

It is of advantage when the blocking means comprises means for accelerating a trigger sleeve. A short reaction time of the blocking means can be obtained by the accelerating means.

If the accelerating means include an accelerating coil spring arranged radially outside on the trigger sleeve, the accelerating means can be realized in a mechanically simple manner. In this way, too, a space-saving mechanical system can be provided.

In this context, it is advantageous when the at least one radially movable nut shell includes an actuating element axially movable with respect to its longitudinal extension which causes radial actuation of the at least one radially movable nut shell with respect to the advancing spindle.

According to another aspect of the invention, the present object is also achieved by a method for operating an infusion pump in which a drive head for an infusion syringe piston of an infusion syringe is advanced by an advancing means, in which a multi-part advancing spindle nut is moved along an advancing spindle for driving the drive head and in which an actuating element of a safety device for preventing inadvertent bolus administration is triggered, when during replacement of the infusion syringe the drive head is moved up to the infusion syringe piston, the actuating element being axially displaced along the advancing spindle according to aspects of the invention, whereby the multi-part advancing spindle nut is moved at least partly radially toward the advancing spindle or moved radially away from the advancing spindle.

By this transformation of movement from the axially directed movement of the actuating element to the radially directed movement of the multi-part advancing spindle nut or parts hereof an extremely efficiently working blocking means of the safety device can be realized.

Preferably the actuating element comprises axially operable sliding sleeves with which the advancing spindle nut is enabled to radially grip on the advancing spindle. Sliding sleeves offer the advantage of being adapted to enclose the advancing spindle nut both radially and axially at least partly in a very generous manner so that an excellent guiding of the sliding sleeves can be achieved especially vis-à-vis one or more nut shells of the advancing spindle nut. Instead of the sliding sleeves also other axial sliding means can be provided, however. For example, such axial sliding means may comprise a sliding ring, a sliding cage or any other axial slide which may also have a linear shape.

Furthermore, it is advantageous when the at least one radially movable nut shell is surrounded radially outside by at least one sliding sleeve, preferably two sliding sleeves, wherein the at least one radially movable nut shell is radially displaceable by at least one sliding sleeve, preferably by two sliding sleeves. In this way, an actuation having an especially simple mechanical design can be provided around the advancing spindle.

It is mentioned in this context that the drive device can be further developed in an extremely advantageous manner, when the blocking means is controllable with a sliding sleeve or preferably at least two sliding sleeves, wherein the at least two sliding sleeves are arranged to be individually drivable and/or sequentially displaceable. The response behavior of the blocking means can be substantially improved in this way.

It plays no ostensible role in this context whether the at least two sliding sleeves are two single sliding sleeves or are one multi-part sliding sleeve divided in the axial direction into two partial sliding sleeves, as long as the partial sliding sleeves can be individually driven and sequentially displaced and the blocking means can thus be controlled in accordance with the invention.

The reliability of the present blocking means can be substantially improved, when the at least one radially movable nut shell has an engaging portion for engaging in a male thread of the advancing spindle and a respective bearing portion for radially bearing on the male thread of the advancing spindle, the engaging portion and the bearing portion being arranged axially in series. Depending on the concrete configuration it may be sufficient, however, when only one single nut shell exhibits such engaging portion.

Especially opening of the advancing spindle nut can be performed by a simple constructional design, when the at least one radially movable nut shell is supported at the end side on an advancing spindle bearing.

Advantageously, the at least one radially movable nut shell is supported at the end side on an advancing slide bearing so that the nut shell can be pivoted to said bearing portion in an especially simple manner and consequently the engaging portion of the nut shell can be especially uncoupled from the male thread.

For this purpose, the nut shell advantageously includes respective pivot bearing portions each of which is arranged ideally at the end side of each of the nut shells.

Of preference, such pivot bearing portion is provided at an end of the respective nut shell facing away from the engaging portion so that a sufficiently long lever arm can be provided between the engaging portion and the pivot bearing portion so as to obtain advantageous coupling and uncoupling of the advancing spindle nut.

A configuration variant further facilitated as to design provides that the at least one radially movable nut shell is arranged to be tilting substantially transversely to its longitudinal extension vis-à-vis the advancing spindle. In this way, radial opening and closing of the advancing spindle nut can be especially easily enabled by structural design so that especially also radially acting spring means can be dispensed with.

The actuating element can be integrated in the present case especially well when the advancing spindle nut has a head area and a foot area the outer diameters of which are larger than an advancing spindle nut zone arranged between the head and foot areas.

Radial actuation of the advancing spindle nut can be designed more advantageously when the head area configures a ramp for axially displaceable sliding sleeves and the foot area configures a counter-bearing for at least one of the axially displaceable sliding sleeves. For example, the multi-part advancing spindle nut can be advantageously closed or engaged in the male thread of the advancing spindle, when at least one of the sliding sleeves is slid axially over the ramp of the advancing spindle nut and accordingly at least one nut shell is moved radially inwards and toward the advancing spindle.

An especially preferred configuration variant provides that an axially displaceable trigger sleeve and an axially displaceable release sleeve exhibit a closing position and an opening position.

With the trigger sleeve the blocking means can be blocked in particular so that the advancing spindle nut is abruptly positively connected to the advancing spindle when the drive head interacts with an infusion syringe piston.

With the release sleeve especially the threaded joint between the advancing spindle and the advancing spindle nut can be released, when the drive device is to be manually operated.

If the advancing means has a parking means for intermediate parking of a sliding sleeve arranged axially adjacent to the advancing spindle nut, the sliding sleeve can advantageously be moved into an opening position.

Moreover, it is of advantage when the advancing means comprises controllable holding solenoids for positioned retaining of sliding sleeves of the advancing spindle nut.

For example, at least one of the sliding sleeves can be retained against the biasing force of a biasing spring in an opening position so that it can spring into a closing position upon deactivation of the corresponding holding solenoid.

The holding solenoids are preferably electrically or electronically controllable.

Accordingly, an advantageous configuration variant provides that the advancing means comprises holding solenoids controllable especially for retaining the advancing spindle nut in an opened operating position.

Cumulatively or alternatively, solenoids controllable in this way can also be provided for retaining the advancing spindle nut in a closed position, for example for temporarily retaining a sliding sleeve in a closing position.

Advantageously, the controllable retaining solenoids for retaining the present sliding sleeves in their respective opening positions are arranged on or integrated in the advancing slide.

It is also of advantage when the drive device includes a means for manually positioning an actuating element of the at least one nut shell.

For example, a sliding sleeve can be re-positioned by manually switching an operating lever in the direction of a solenoid, while at the same time the solenoid is activated by operating the operating lever.

Advantageously, the positioning means can include a positioning shaft for positioning sliding sleeves of the advancing spindle nut so that manual actuation especially of the advancing spindle nut is easily possible in terms of structural design via the means for manual positioning which is arranged, for example, on the rear side of the drive head distant from the advancing means.

In this context, it is mentioned once again that the drive head for a piston plate of the infusion syringe offers a counter-bearing to the advancing means. The piston plate of the infusion syringe is supported by the same. The infusion syringe is linearly squeezed out by an internal movement of the advancing means. The piston plate of the infusion syringe is safely fixed to the drive head with two spring-loaded fixing brackets of a retaining claw. The fixing brackets further retain the piston plate of even most different infusion syringes at a diaphragm plate of the drive head by form and force closure, thus ensuring prompt start-up behavior as well as axial fixing of the syringe piston even with a prevailing vacuum in the infusion syringe. The diaphragm plate moves into the drive head by contacting the piston plate, wherein two light barriers of a double switching threshold means are successively passed. With the two light barriers the form closure between the advancing spindle nut and the advancing spindle as well as the play-free approach of the drive head to the piston plate are controlled without a bolus administration being produced.

Furthermore, a force sensor for determining the prevailing drive force is provided in the drive head. Upon actuation of the operating lever arranged on the rear side of the drive head, the retaining claw is opened and the form closure between the advancing spindle nut and the advancing spindle is reversed. The operation of the operating lever is preferably detected with appropriate micro-switches and the holding solenoids are controlled by the latter. The opening of the retaining claw moreover causes the spring-loaded diaphragm plate to move out of the drive head.

Advantageously, an excellent automatic infusion syringe fixation regarding an infusion pump is achieved with the present invention. The invention especially excels by the option of the drive head being adapted to be moved particularly quickly toward the piston plate. In this case, the user can even better determine the duration of replacement of the infusion syringe, which is advantageous in particular in critical treatment situations. Nevertheless, it can be ensured in an especially reliable manner that almost bolus-free insertion of the infusion syringe and prompt start-up behavior are permitted.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

The drive device 1 of an infusion pump 2 shown in FIGS. 1 to 5 substantially comprises a drive head 3 for moving a piston 4 of an infusion syringe 5 mounted on the infusion pump 2 and an advancing means 6 for the drive head 3.

Figure 2:
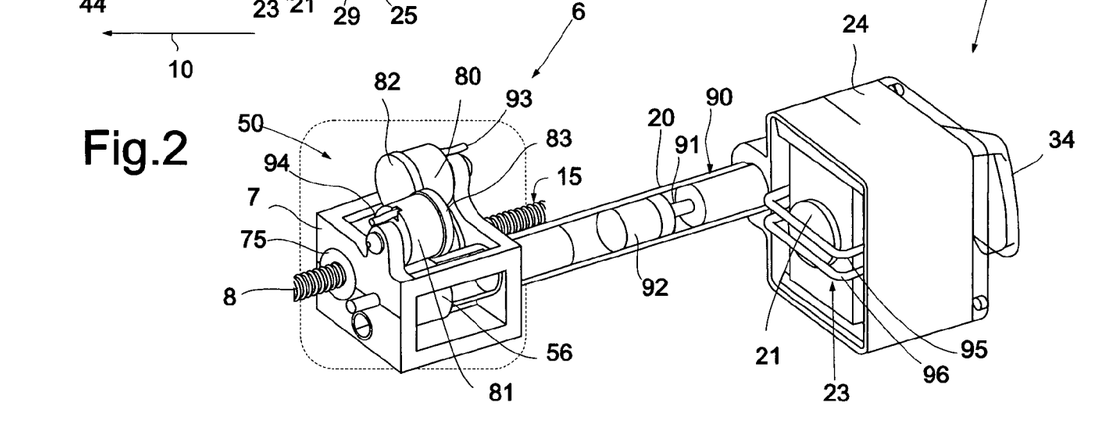
FIG. 2 a schematic view of a drive device of the infusion pump from FIG. 1 comprising an infusion syringe piston drive head and an advancing means for the same.

The advancing means 6 substantially comprises an advancing slide 7, an advancing spindle 8 and a multi-part advancing spindle nut 9. Moreover it comprises an advancing motor and a corresponding gear system not shown in the present case, however. The advancing means 6 converts a linear infeed motion of the drive head 3.

In the advancing slide 7 the linear guide and the anti-torsion protection of the drive head 3 are ensured.

The multi-part advancing spindle nut 9 and the advancing slide 7, resp., can be forwardly driven in the piston driving direction 10 when the direction of rotation of the advancing spindle 8 is appropriately chosen, wherein especially the multi-part advancing spindle nut 9 is moved axially along the longitudinal extension 11 of the advancing spindle 8.

The multi-part advancing spindle nut 9 in this case comprises a first radially movable nut shell 12 and a second radially movable nut shell 13, as will be described in more detail later. At any rate, the radially movable nut shells 12 and 13 can ensure axial form closure with the advancing spindle 8 and also reverse the same, however.

The term "radially" characterizes a radial direction of movement 14 substantially transversely to the longitudinal extension 11 of the advancing spindle 8. The advancing spindle 8 has a male thread 15 by which the multi-part advancing spindle nut 9 can be positively connected.

The drive head 3 is fastened to the advancing slide 7 with a retaining arm 20. The drive head 3 comprises a diaphragm plate 21 for bearing a piston plate 22 of the infusion syringe piston 4 thereon. Here the piston plate 22 is fixed to the drive head 3 with the retaining claw 23 so that a positive connection between the infusion syringe piston 4 and the drive head 3 is guaranteed.

In its drive head housing 24 the drive head 3 accommodates a piston plate sensor 25 which, on the one hand, comprises a spring 26 biased axially displaceable transmitter element 27 and, on the other hand, a double switching threshold means 28 adapted to be influenced by the transmitter element 27 and having a first light barrier 29 and a second light barrier 30.

On the one hand, the function of a drive gear 31 of the retaining claw 23 can be controlled with the piston plate sensor 25. On the other hand, the function of the advancing means 6 can be influenced by the piston plate sensor 25, as will be described in more detail hereinafter. For this purpose, the piston plate sensor 25 is connected to a control 33 of the advancing means 6 via an appropriate signal line 32.

Further provided on the drive head 3 is a manually operable operating lever 34 by which the functions of the retaining claw 23 and the advancing means 6 can be additionally manually actuated. For mechanically actuating the advancing means 6 via the operating lever 34 the latter is guided from the drive head 3 through the retaining arm 20 up to the advancing means 6.

Figure 1:
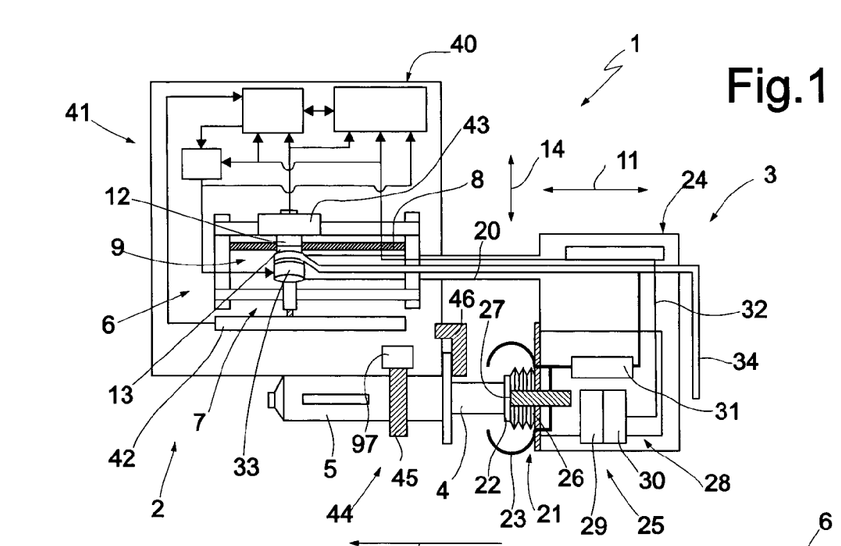
FIG. 1 a schematic view of an infusion pump comprising an infusion syringe arranged on the same.

The infusion pump 2 schematically illustrated especially in FIG. 1 includes an infusion pump housing 40 in which, apart from the advancing means 6, also further functional parts such as further control means 41 are accommodated, which will be referred to only in so far as they are essential to the present invention. The control means 41, for example, comprise a sensor 42 for detecting the correct mounting position of the infusion syringe 5 and a form closure sensor 43 for checking a form closure state between the multi-part advancing spindle nut 9 and the advancing spindle 8. Furthermore, a seat 44 for the infusion syringe 5 is provided to be accessible from outside at the infusion pump housing 40, the seat comprising a clamping bracket 45 for radially securing the infusion syringe 5 and a clamping lug 46 for axially securing the infusion syringe 5.

Advantageously the infusion pump 2 further comprises a safety device 50 to prevent inadvertent bolus administration to a patient especially during replacement of the infusion syringe when a used infusion syringe 5 has to be replaced with a new infusion syringe 5 (cf. especially FIG. 2).

The safety device 50 in turn comprises a blocking means 51 adapted to be automatically triggered with a piston plate sensor 25 for blocking a manual infeed motion of the drive head 3 in the piston driving direction 10 which directly comprises the multi-part advancing spindle nut 9 according to aspects of the invention.

The blocking means 51 advantageously comprises an axially movable actuating element 52 which by way of example in this case comprises at least one axially movable releasing sleeve 53 that is arranged concentrically around the two nut shells 12 and 13 of the advancing spindle nut 9. The releasing sleeve 53 is movably supported radially outside on the advancing spindle nut 9 in the longitudinal extension 11 of the advancing spindle 8.

So that the blocking means 51 can be activated extremely quickly it exhibits means 54 for accelerating the triggering sleeve 53, the accelerating means 54 being configured in a structurally simple manner by a coil spring 55 which in turn is supported radially outside on the triggering sleeve 53.

Furthermore, the operating element 52 includes a release sleeve 56 which may equally be disposed to be axially movable and concentric around the two nut shells 12 and 13 of the advancing spindle nut 9.

In this respect, the two sliding sleeves 53 and 56 are supported to be axially movable also with respect to the longitudinal extension 57 of the two radially movable nut shells 12 and 13. The two sliding sleeves 53, 56 are individually driven and sequentially movable, as will be described in greater detail hereinafter.

Figure 3A:
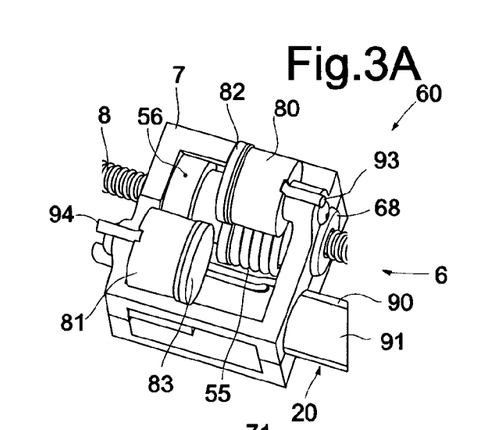
FIG. 3A a schematic detail view of the advancing means from FIG. 2 in a first operating position selected by way of example.
Figure 3B:
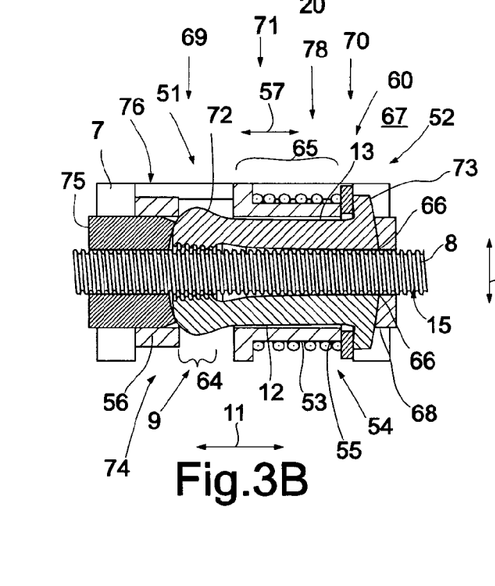
FIG. 3B a schematic view of a longitudinal section of the detail view from FIG. 3A.

For better comprehension of the functioning of the present operating element 52 of the advancing spindle nut 9, in FIGS. 3A and 3B a first operating position 60 of the advancing means 6 is exemplified in which the two nut shells 12 and 13 are not in positive engagement with the male thread 15 of the advancing spindle 8. In said first operating position 60 the drive head 3 can be quickly moved toward the piston plate 22 with a manual infeed motion in the piston driving direction 10. This operating position 60 can especially be chosen when the infusion syringe is replaced at the infusion pump 2.

Figure 4A:
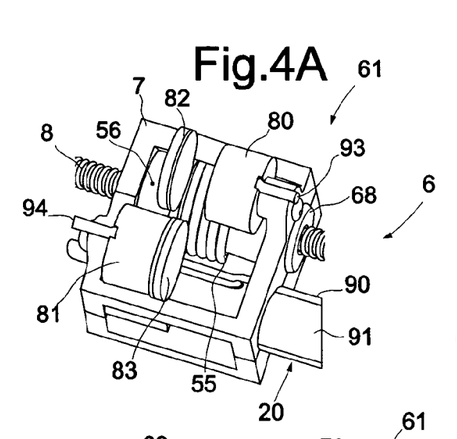
FIG. 4A a further schematic detail view of the advancing means from FIGS. 2 and 3 in a second operating position selected by way of example.
Figure 4B:
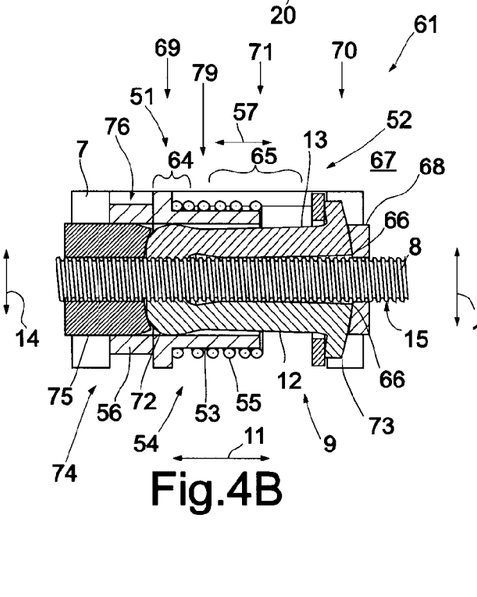
FIG. 4B a schematic view of a longitudinal section of the detail view from FIG. 4A.

In a second operating position 61 of the advancing means 6 exemplified in the FIGS. 4A and 4B the blocking means 51 is triggered and the advancing means 6 is blocked as such by the advancing spindle nut 9 so that no further manual infeed motion of the drive head 3 in the piston driving direction 10 is possible. In this respect, the risk that the diaphragm plate 21 critically abuts against the piston plate 22 and consequently bolus administration possibly dangerous to a patient is inadvertently carried out is excluded.

Figure 5A:
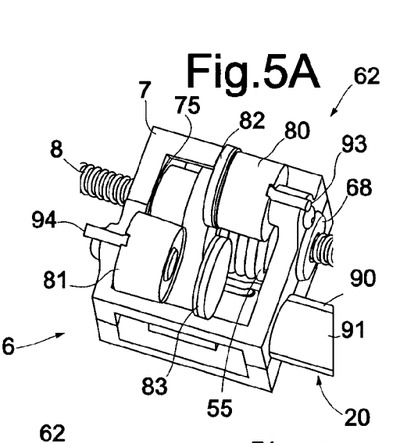
FIG. 5A an additional schematic detail view of the advancing means from FIGS. 3 and 4 in a third operating position selected by way of example.
Figure 5B:
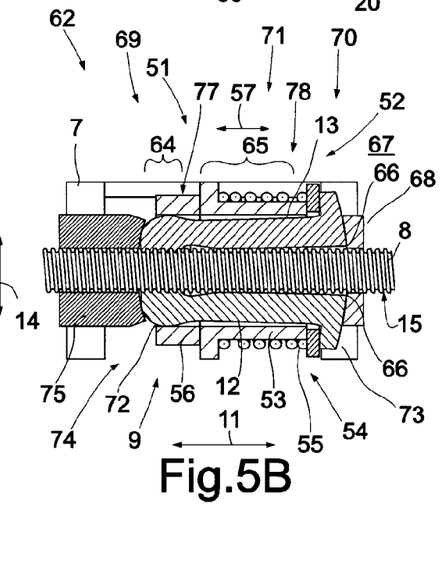
FIG. 5B a schematic view of a longitudinal section of the detail view from FIG. 5A.

Finally, in a further third operating position 62 chosen by way of example regarding the FIGS. 5A and 5B the advancing means 6 is in basic operation in which the drive head 3 is successively driven by the advancing means 6 in the piston driving direction 10 and in which thus a desired infusion therapy can be executed in a way known per se with the infusion pump 2.

Each of the two radially movable nut shells 12 and 13 has an engaging area 64 for engaging in the male thread 15 of the advancing spindle 8. In so far a positive connection between the nut shells 12 and 13 of the advancing spindle nut 9 and the male thread 15 of the advancing spindle 8 can be produced above the respective engaging area 64 of the nut shells 12 and 13, resp., when said engaging area 64 is properly moved or retained radially in the direction of the advancing spindle 8. This is the case, for example, with the two operating positions 61 and 62. Moreover, the two radially movable nut shells 12 and 13 further include a supporting area 65 with which the nut shells 12 and 13 at most can rest radially on the male thread 15 but cannot engage with the same. The engaging area 64 and the supporting area 65 are arranged axially in series.

In order to be able to radially incline each of the two radially movable nut shells 12, 13 with the two sliding sleeves 53, 56 vis-à-vis the advancing spindle 8 about a tilting axis 66 extending substantially transversely to the longitudinal extension 57 of the respective nut shell 12 and 13, resp., each of the two nut shells 12 and 13 is supported at its end side 67 on an advancing slide bearing 68. According to the representation of the FIGS. 3B, 4B and 5B, the tilting axis 66 extends normal to the drawing plane.

Moreover, the advancing spindle nut 9 includes a head area 69 and a foot area 70 the respective outer diameters of which are larger than an interposed advancing spindle nut zone 71, the head area 69 forming a slide-on ramp 72 for the two axially movable sliding sleeves 53 and 56 and the foot area 70 forming a counter-bearing 73 for the two axially movable sliding sleeves 53 and 56.

At an advancing spindle nut end 74 facing the advancing slide bearing 68 a parking means 75 supported on the advancing slide 7 for the release sleeve 56 is provided, wherein the parking means 75 is placed axially adjacent to the advancing spindle nut 9. When the release sleeve 56 is slipped onto the seat of the parking means 75 and is parked adjacent to the advancing spindle nut 9, the release sleeve 56 is provided in an opening position 76. This is the case with the two operating positions 60 and 61. In the third operating position 62 the release sleeve 56 is displaced onto the ramp 72 and is accordingly provided in a closing position 77.

The release sleeve 53 is provided in each of the two operating positions 60 and 62 in its own opening position 78 in which the trigger sleeve 53 is facing the counter-bearing 73 more closely than the ramp 72. Merely in the operating position 61 the trigger sleeve 53 is provided in a closing position 79 assigned thereto.

Moreover, the advancing means 8 comprises a first holding solenoid 80 and a second holding solenoid 81 arranged above the advancing slide 7 in this embodiment.

The first holding solenoid 80 is associated with the release sleeve 53 and accordingly it may correspond to a magnetic plate 82 of the release sleeve 53. For this purpose, the magnetic plate 82 is placed ahead of the first holding solenoid 80 and is supported to be axially movable while being coupled to the release sleeve 53. In the two operating positions 60 and 62 the first holding solenoid 80 is supplied with current so that it can keep contact with the magnetic plate 82 and thus can also retain the release sleeve 53 in its opening position 78. In the operating position 61 the magnetic plate 82 is spaced apart from the first holding solenoid 80 to which no current is fed.

Accordingly, the second holding solenoid 81 is associated with the release sleeve 56 and it may correspond to a magnetic plate 83 of the release sleeve 56, said magnetic plate 83 being placed ahead of the second holding solenoid 81 for this purpose. The magnetic plate 83 is axially displaced jointly with the release sleeve 56, as it is coupled thereto. In this respect, in the operating positions 60 and 61 the magnetic plate 83 is in contact with the second current-fed holding solenoid 81, while in the operating position 62 it is arranged distant from the second holding solenoid 81 to which no current is fed.

When it is desired or necessary to replace the infusion syringe, the infusion is stopped. Subsequently the operating lever 34 is actuated at the drive head 3. By actuating the operating lever 34 the spring 92 loaded release sleeve 56 is moved in the direction of the second holding solenoid 81 by the retaining arm 20 designed as tube 90 (cf. FIG. 3) via an inner fixing shaft 91. Said actuation is additionally detected by a micro-switch comprising a sensor not shown here, thereby the two holding solenoids 80 and 81 being supplied with current via appropriate electric cables 93 and 94 and the two sliding sleeves 53 and 56 being separated from each other. Accordingly, the two nut shells 12 and 13 open. Also the fixing brackets 95 and 96, resp., of the retaining claw 23 open due to the actuation of the operating lever 34. The form closure between the advancing spindle 8 and the advancing spindle nut 9 is reversed according to the first operating position 60 and the drive head 3 can be brought into a deployed position (not denoted here) opposite to the piston driving direction 10.

Subsequently, the clamping bracket 45 is opened and appropriately swiveled so that the seat 44 is easily accessible. A potentiometer 97 identifies the state of the clamping bracket 45 inside the infusion pump housing 40. The infusion syringe 5 to be replaced can be removed now and the new infusion syringe 5 can be inserted into the seat. The infusion syringe wings of the infusion syringe 5 to be inserted are secured to the clamping lug 46 so that the new infusion syringe 5 is axially fixed to the infusion syringe pump 2. In this context, also the clamping bracket 45 is closed again so that the infusion syringe 5 is also radially fixed. With the potentiometer 97 on the clamping bracket 45 the infusion syringe diameter is directly measured.

Now the drive head 3 can be guided up to the piston plate 22 in accordance with the fill level of the infusion syringe 5 and thus also the position of the piston 4. So that larger distances between the drive head 3 and the piston plate 22 can be overcome more quickly, this can be performed by manual infeed motion in the piston driving direction 10, as the two radially movable nut shells 12 and 13 are not engaged in the male thread 15 of the advancing spindle 8, as this is shown in the first operating position 60 according to FIGS. 3A and 3B. In the first operating position 60 the two holding solenoids 80 and 81 are supplied with current, the sliding sleeves 53 and 56 are arranged to be separated from each other and the two nut shells 12 and 13 are radially opened. Moreover, the retaining claw 23 is opened on the drive head 3.

As soon as the diaphragm plate 21 enters into contact with the piston plate 22, the transmitter element 27 especially moves inwardly into the drive head 3. Inside the drive head casing 24 the transmitter element 27 successively passes the two light barriers 29 and 30 of the double switching threshold unit 28.

When passing through the first light barrier 29 the current supply to the first holding solenoid 80 is disconnected and the release sleeve 53 is pushed over the ramps 72 of the two radially movable nut shells 12 and 13 with the further spring 92, thereby the advancing spindle nut 9 positively engaging with the engaging areas 64 in the male thread 15 of the advancing spindle 8. Thus the advancing means 6 blocks, as is represented in the second operating position 61 according to FIGS. 4A and 4B. Manual infeed motion in the piston driving direction 10 is suddenly suppressed hereby.

However, the advancing means 6 now automatically continues traveling until the transmitter element 27 passes through the second light barrier 30. The second light barrier 30 is required here, as the change of position of the closed nut shells 12 and 13 with their engaging areas 64 vis-à-vis the advancing spindle 8 is dependent on the reaction rate of the first holding solenoid 80 and the motion speed of the drive head 3 up to the piston plate 22. It is further possible that upon closing the advancing spindle nut 9 the two radially movable nut shells 12 and 13 merely rest on the thread flanks of the male thread 15 and the engaging area 64 of the advancing spindle nut 9 thus has not efficiently engaged in the male thread 15. However, by a short travel up to the second light barrier 30 the advancing spindle nut 9 can properly engage in the advancing spindle 8. Upon reaching the second light barrier 30 the linear position of the drive device 1 is then defined. With this reference travel in accordance with the invention the advancing means 6 is provided in the second operating position 61 in which the first holding solenoid 80 is currentless, but the second holding solenoid 81 is supplied with current. Both sliding sleeves 53 and 56 are displaced to the left in the advancing slide 7 and the two nut shells 12 and 13 are radially closed. The retaining claw 23 on the drive head 3 is still opened.

The drive head 3 traces the aligned path from the second light barrier 30 up to a force sensor (not explicitly shown here) with which correct bearing of the piston plate 22 on the main drive head 3 is detected and signaled.

The second holding solenoid 81 is switched to be currentless, the release sleeve 56 is displaced into its closing position 77, the retaining claw 23 closes and the fixing brackets 95 and 96 bear on the piston plate 22 of the infusion syringe 5 with form and force closure. The infusion syringe 5 is now caught safely and free from play. With the clamping bracket 45 and the potentiometer 97 already the infusion syringe diameter has been measured so that on a display (not shown here) of the infusion pump 2 a selection of appropriate infusion syringes 5 is suggested. After confirmation of the valid infusion syringe 5 the desired infusion therapy can be entered and the infusion can now be started, wherein the advancing means 6 is provided in the third operating position 62 according to FIGS. 5A and 5B. In the third operating position 62 the advancing means 6 is thus locked. This means that the two holding solenoids 80, 81 are currentless. It is especially advantageous that here a powerless state is provided regarding the two holding solenoids 80, 81 so that the third operating state 62 is functioning even without supplying the holding solenoids 80, 81 with current. The two sliding sleeves 53, 56 are displaced to the right within the advancing slide 7, because the further spring 92 is designed to be stronger than the coil spring 55. The two nut shells remain radially closed just as the retaining claw 23 on the drive head 3 is equally closed.

Figure 6:
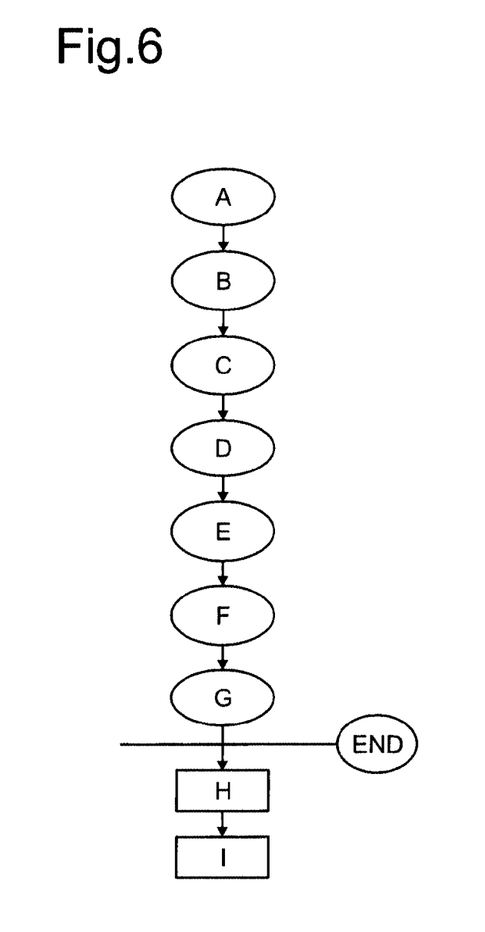
FIG. 6 a schematic view of a process cycle for preventing inadvertent bolus administration to a patient.

In the representation according to FIG. 6 a preferred process cycle is illustrated as regards the drive device 1 according to aspects of the invention. Preferably, it starts with step A in which the advancing spindle nut 9 and the retaining claw 23 are manually opened. Step B follows thereafter in which the retaining claw 23 locks in its opened position according to the representation of FIG. 1. As regards step C, the advancing spindle nut 9 remains in its opened position by the two holding solenoids 80 and 81. Subsequently, by step D the drive head 3 is manually displaced in the desired manner. In step E the diaphragm plate 21 is manually moved onto the piston plate 22. In accordance with step F the first light barrier 29 is actuated with the leading transmitter element 27, the switching point being located approx. 3.5 mm ahead of the piston plate 22. In step G a signal of the first light barrier 29 radially closes the advancing spindle nut 9 by switching off the first holding solenoid 80 and the blocking means 51 blocks a further manual infeed motion of the drive head 3. At this point the actual process for preventing inadvertent bolus administration is completed. After that step H follows in which the drive head 3 now is automatically further advanced onto the piston plate 22 with the aid of the second light barrier 30. And in step I the retaining claw 23 closes again.

It is understood that the afore-explained embodiment merely is a first configuration of the drive device according to aspects of the invention. In so far the configuration of the invention is not restricted to this embodiment.

All features disclosed in the application documents are claimed as being essential to the invention, if they are novel vis-à-vis the state of the art either individually or in combination.

The invention claimed is:

1. A drive device of an infusion syringe piston drive head for moving an infusion syringe piston comprising:
    an advancing means including an advancing slide, an advancing spindle and a multi-part advancing spindle nut including at least one radially movable nut shell; and
    a blocking means adapted to be automatically triggered by a control sensor and configured to block an infeed motion of the drive head in which the advancing slide can be driven on the advancing spindle by the advancing spindle nut and in which the drive head is arranged on the advancing slide, wherein the blocking means adapted to be automatically triggered by the control sensor comprises the multi-part advancing spindle nut configured to block the infeed motion of the drive head on the advancing spindle and an axially displaceable trigger sleeve that at least partially surrounds a radial outside of the advancing spindle nut.

2. The drive device according to claim 1, wherein the blocking means comprises means for accelerating the trigger sleeve, the accelerating means including an accelerating coil spring arranged radially outside on the trigger sleeve.

3. The drive device according to claim 1, wherein the blocking means is controllable by one sliding sleeve.

4. The drive device according to claim 1, wherein the blocking means is controllable by at least two sliding sleeves, wherein the at least two sliding sleeves are arranged to be individually drivable and/or to be sequentially movable.

5. The drive device according to claim 1, wherein the at least one radially movable nut shell includes an actuating element axially displaceable with respect to a longitudinal extension of the at least one radially movable nut shell which causes radial actuation of the at least one radially movable nut shell with respect to the advancing spindle.

6. The drive device according to claim 1, wherein the at least one radially movable nut shell is at least partly surrounded radially outside by at least one sliding sleeve, wherein the at least one radially movable nut shell is radially displaceable by the at least one sliding sleeve.

7. The drive device according to claim 1, wherein the at least one radially movable nut shell is at least partly surrounded radially outside by two sliding sleeves, wherein the at least one radially movable nut shell is radially displaceable by the two sliding sleeves.

8. The drive device according to claim 1, wherein the at least one radially movable nut shell includes an engaging area for engaging in a male thread of the advancing spindle and a supporting area for radially bearing on the male thread of the advancing spindle, wherein the engaging area and the supporting area are arranged axially in series.

9. The drive device according to claim 1, wherein the at least one radially movable nut shell is supported at an end side on an advancing slide bearing.

10. The drive device according to claim 1, wherein the at least one radially movable nut shell is arranged to be tilting vis-à-vis the advancing spindle substantially transversely to a longitudinal extension of the at least one radially movable nut shell.

11. The drive device according to claim 1, wherein the advancing means includes a parking means for intermediately parking a sliding sleeve arranged axially adjacent to the advancing spindle nut.

12. The drive device according to claim 1, wherein the control sensor is arranged in the drive head so that the blocking means can be automatically triggered upon actuation of the control sensor by a piston plate of the infusion syringe piston.

13. An infusion pump comprising the drive head for moving the infusion syringe piston of an infusion syringe arranged on the infusion pump, comprising the advancing means for driving the drive head and comprising a safety device for preventing inadvertent bolus administration, wherein the infusion pump includes the drive device in accordance with claim 1.

14. A drive device of an infusion syringe piston drive head for moving an infusion syringe piston comprising:
   an advancing means including an advancing slide, an advancing spindle and a multi-part advancing spindle nut including at least one radially movable nut shell; and
   a blocking means adapted to be automatically triggered by a control sensor and configured to block an infeed motion of the drive head in which the advancing slide can be driven on the advancing spindle by the advancing spindle nut and in which the drive head is arranged on the advancing slide, wherein the blocking means adapted to be automatically triggered by the control sensor comprises the multi-part advancing spindle nut configured to block the infeed motion of the drive head on the advancing spindle and an axially displaceable trigger sleeve that at least partially surrounds a radial outside of the advancing spindle nut, and wherein the advancing spindle nut has a head area and a foot area, respective outer diameters of which are larger than a diameter of an advancing spindle nut zone disposed between the head and foot areas.

15. The drive device according to claim 14, wherein the head area comprises a ramp for axially displaceable sliding sleeves and the foot area comprises a counter-bearing for at least one of the axially displaceable sliding sleeves.

16. A drive device of an infusion syringe piston drive head for moving an infusion syringe piston comprising:
   an advancing means including an advancing slide, an advancing spindle and a multi-part advancing spindle nut including at least one radially movable nut shell; and
   a blocking means adapted to be automatically triggered by a control sensor and configured to block an infeed motion of the drive head in which the advancing slide can be driven on the advancing spindle by the advancing spindle nut and in which the drive head is arranged on the advancing slide, wherein the blocking means adapted to be automatically triggered by the control sensor comprises the multi-part advancing spindle nut configured to block the infeed motion of the drive head on the advancing spindle wherein the advancing means comprises controllable holding solenoids for maintaining the advancing spindle nut in an opened operating position.

17. A method of operating an infusion pump, the method comprising the steps of:
   advancing, with an advancing means, a drive head for an infusion syringe piston of an infusion syringe, wherein the advancing means comprises an advancing slide on which the drive head is arranged;
   moving a multi-part advancing spindle nut along an advancing spindle configured to drive the advancing slide on which the drive head is arranged;
   triggering, with a sensor, a blocking means of a safety device configured to prevent inadvertent bolus administration and to block an infeed motion of the drive head, when the drive head is moved up to the infusion syringe piston during replacement of the infusion syringe, and wherein the blocking means comprises the multi-part advancing spindle nut adapted to block the infeed motion of the drive head on the advancing spindle; and
   axially displacing an actuating element of at least one radially movable nut shell along the advancing spindle with respect to a longitudinal extension of the radially movable nut shell, such that the multi-part advancing spindle nut is radially moved at least partly toward the advancing spindle or away from the advancing spindle.

* * * * *